(12) United States Patent
Haviv

(10) Patent No.: US 10,682,387 B2
(45) Date of Patent: Jun. 16, 2020

(54) ORAL OCTREOTIDE ADMINISTERED IN COMBINATION WITH OTHER THERAPEUTIC AGENTS

(71) Applicant: Chiasma, Inc., Waltham, MA (US)

(72) Inventor: Asi Haviv, Gan-Shlomo (IL)

(73) Assignee: Chiasma, Inc., Needham, MA (US)

(*) Notice: Subject to any disclaimer, the term of this patent is extended or adjusted under 35 U.S.C. 154(b) by 0 days.

(21) Appl. No.: 15/972,557

(22) Filed: May 7, 2018

(65) Prior Publication Data
US 2019/0091285 A1    Mar. 28, 2019

Related U.S. Application Data

(63) Continuation of application No. 14/965,318, filed on Dec. 10, 2015, now abandoned.

(60) Provisional application No. 62/090,130, filed on Dec. 10, 2014.

(51) Int. Cl.
| | | |
|---|---|---|
| A61K 38/12 | (2006.01) | |
| A61K 38/08 | (2019.01) | |
| A61K 45/06 | (2006.01) | |
| C07K 7/06 | (2006.01) | |
| A61K 38/31 | (2006.01) | |
| A61K 31/48 | (2006.01) | |
| A61K 31/135 | (2006.01) | |
| A61K 31/4745 | (2006.01) | |
| A61K 38/27 | (2006.01) | |

(52) U.S. Cl.
CPC ............ *A61K 38/12* (2013.01); *A61K 31/135* (2013.01); *A61K 31/4745* (2013.01); *A61K 31/48* (2013.01); *A61K 38/08* (2013.01); *A61K 38/27* (2013.01); *A61K 38/31* (2013.01); *A61K 45/06* (2013.01); *C07K 7/06* (2013.01)

(58) Field of Classification Search
None
See application file for complete search history.

(56) References Cited

U.S. PATENT DOCUMENTS

| | | | |
|---|---|---|---|
| 5,393,738 | A | 2/1995 | Vonderscher et al. |
| 8,133,863 | B2 | 3/2012 | Maggio |
| 8,329,198 | B2 | 12/2012 | Salama et al. |
| 8,535,695 | B2 | 9/2013 | Salama et al. |
| 8,822,637 | B2 | 9/2014 | Albert et al. |
| 2007/0219131 | A1 | 9/2007 | Ben-Sasson |
| 2009/0220611 | A1 | 9/2009 | Dargelas et al. |
| 2010/0105627 | A1 | 4/2010 | Salama et al. |
| 2010/0151033 | A1 | 6/2010 | Ahlheim et al. |
| 2011/0142800 | A1 | 6/2011 | Kidron et al. |
| 2016/0193285 | A1 | 7/2016 | Haviv |

FOREIGN PATENT DOCUMENTS

| | | |
|---|---|---|
| WO | 1993017037 A1 | 9/1993 |
| WO | 2005041901 A2 | 5/2005 |
| WO | 2005046642 A1 | 5/2005 |
| WO | 2006013369 A2 | 2/2006 |
| WO | 2006097793 A2 | 9/2006 |
| WO | 2007095091 A2 | 8/2007 |
| WO | 2010032140 A2 | 3/2010 |
| WO | 2016/094662 A1 | 6/2016 |

OTHER PUBLICATIONS

Reid, Tirissa J. et al, "Igf-1 levels across the spectrum of normal to elevatd in acromegaly: relationship to insulin sensitivyt, markers of cardiovascular risk and body composition." Pituitary (2015) 18 p. 808-819.*

Duarte et al. "Impact of clomiphene citrate on IGF-1 and testosterone levels in acromegalic patients non controlled by conventional therapy." Endocrine Reviews, Endocrine Society's 96th Annual Meeting and Expo (2014).

Katznelson et al. "Acromegaly: an endocrine society clinical practice guideline." Journal of Clinical Endocrinology and Metabolism (2014): vol. 99, No. 11, 3933-3951.

Manjila et al. "Pharmacological management of acromegaly: a current perspective." Neurological Focus (2010): vol. 29, No. 4, 1-9.

Neggers et al. "Long-Term efficacy and safety of pegvisomant in combination with long-acting somatostatin analogs in acromegaly." Journal of Clinical Endocrinology and Metabolism (2014): vol. 99, No. 10, 3644-3652.

Shimon et al. "Estrogen treatment for acromegaly." Pituitary (2012): vol. 15, No. 4, 601-607.

Suda et al. "Efficacy of combined octreotide and cabergoline treatment in patients with acromegaly: a retrospective clinical study and review of the literature." Endocrine Journal (2013): vol. 60, No. 4, 507-515.

"Dad found drug for sick daughter using internet research" The Sentinel, Jul. 22, 2010.

"Octreotide for a Possible Cure for IIH" Facebook; Retrieived from www.facebook.com/pages/Octreotide-for-a-Possible-Cure-for-IIH on Mar. 3, 2015.

Adelman et al. "Acromegaly: the disease, its impact on patients, and managing the burden of long-term treatment" International Journal of General Medicine (2013) vol. 6, pp. 31-38.

Besson et al. "Sclerotherapy With or Without Octreotide for Acute Variceal Bleeding" The New England Journal of Medicine (1995) vol. 333, No. 9, pp. 555-560.

Biousse et al. "Update on the pathophysiology and management of idiopathic intracranial hypertension" J Neurol Neurosurg Psychiatry (2012) Bol 83, pp. 488-494.

(Continued)

*Primary Examiner* — Fred H Reynolds
(74) *Attorney, Agent, or Firm* — Goodwin Proctor LLP

(57) ABSTRACT

This invention relates to combination therapy of a subject suffering from acromegaly. The method of treatment comprises administration to the subject of a therapeutically effective amount of oral somatostatin receptor ligand (SRL) e.g. octreotide in combination with a therapeutically effective amount of a dopamine agonist and/or a growth hormone receptor antagonist and/or a selective estrogen receptor modulator (SERM) and/or a $2^{nd}$ somatostatin receptor ligand (SRL).

3 Claims, No Drawings

(56) References Cited

OTHER PUBLICATIONS

Chanson et al. "Comparison of octreotide acetate LAR and lanreotide SR in patients with acromegaly" Clinical Endocrinology (2000) vol. 53, pp. 577-586.
Costa et al. "Octreotide—A Review of its Use in Treating Neuroendocrine Tumours" European Oncology & Haematology, (2013) vol. 9, No. 2, pp. 105-109.
Deftereos et al. "Treatment of idiopathic intracranial hypertension: Is there a place for octreotide?" Cephalalgia (2011) vol. 31, No. 16, pp. 1679-1680.
Dorkoosh et al. "Peroral Absorption of Octreotide in Pigs Formulated in Delivery Systems on the Basis of Superporous Hydrogel Polymers" Pharmaceutical Research (2002) vol. 19, No. 10 pp. 1532-1536.
Drewe et al. "Enteral absorption of octreotide: absorption enhancement by polyoxyethylene-24-cholesterol ether" Br. J. Pharmacol. (1993) vol. 108, pp. 298-303.
Duarte et al. "Clomiphene citrate for treatment of acromegaly not controlled by conventional therapies" Journal of Clinical Endocrinology Metabolism (2015) doi: 10.1210/jc2014-3913 pp. 1-8.
Fricker et al. "Permeation enhancement of octreotide by specific bile salts in rats and human subjects: in vitro, in vivo correlations" British Journal of Pharmacology (1996)vol. 117, pp. 217-223.
Geer, Richard J., et al. "Efficacy of octreotide acetate in treatment of severe postgastrectomy dumping syndrome." Annals of surgery 212.6 (1990): 678.
Giustina et al. "A consensus on the medical treatment of acromegaly" Nature Reviews Endocrinology (2014) vol. 10, pp. 243-248.
Hemingway et al. "The effects of sandostatin (Octreotide, SMS 201-995) infusion on splanchnic and hepatic blood flow in an experimental model of hepatic metastases" Br. J. Cancer (1992) vol. 65, pp. 396-398.
Jenkins et al. "Pharmacokinetics of Octreotide in Patients with Cirrhosis and Portal Hypertension; Relationship Between the Plasma Levels of the Analogue and the Magnitude and Duration of the Reduction in Corrected Wedged Hepatic Venous Pressure" HPB Surgery (1998) vol. 11, pp. 13-21.
Köhler, E., et al. "Absorption of an aqueous solution of a new synthetic somatostatin analogue administered to man by gavage." European journal of clinical pharmacology 33.2 (1987): 167-171.
Lueck, Christian J., and Gawn G. McIlwaine. "Interventions for idiopathic intracranial hypertension." The Cochrane Library (2009).
Lustig, R. H., et al. "A multicenter, randomized, double-blind, placebo-controlled, dose-finding trial of a long-acting formulation of octreotide in promoting weight loss in obese adults with insulin hypersecretion." International Journal of Obesity 30.2 (2006): 331-341.
McCormick, P. Aiden, et al. "Cardiovascular effects of octreotide in patients with hepatic cirrhosis." Hepatology 21.5 (1995): 1255-1260.
Melmed et al. "OR17-5 Efficacy and Safety of Oral Octreotide in Acromegaly: Results of a Multicenter Phase III Trial in 155 Patients" Abstracts—Orals, Poster Preview Presentations, and Posters OR17—From Genetics to Clinical Trials in Pituitary Disease Clinical/Translational, Sunday, Jun. 22, 2014.
Melmed, Shlomo. "New therapeutic agents for acromegaly." Nature Reviews Endocrinology 12.2 (2016): 90-98; Advanced online publication Nature Reviews Endocrinology Nov. 27, 2015, pp. 1-9.
Møller, Søren, et al. "Effect of octreotide on systemic, central, and splanchnic haemodynamics in cirrhosis." Journal of hepatology 26.5 (1997): 1026-1033.
Panagopoulos, G. N., et al. "Octreotide: a therapeutic option for idiopathic intracranial hypertension." Neurol Neurophysiol Neurosci 1 (2007): 1-6.
Sanchez, George A., Nisa Kubiliun, and Jamie S. Barkin. "Variceal bleeding and long-acting octreotide: a new addition to the armamentarium?." Digestive diseases and sciences 53.11 (2008): 3046-3047.
Spahr, Laurent, et al. "A 3-month course of long-acting repeatable octreotide (sandostatin LAR) improves portal hypertension in patients with cirrhosis: a randomized controlled study." The American journal of gastroenterology 102.7 (2007): 1397-1405.
Suda, Kentaro, et al. "Efficacy of combined octreotide and cabergoline treatment in patients with acromegaly: a retrospective clinical study and review of the literature." Endocrine journal 60.4 (2013): 507-515.
Thanou, M., et al. "Intestinal absorption of octreotide: N-trimethyl chitosan chloride (TMC) ameliorates the permeability and absorption properties of the somatostatin analogue in vitro and in vivo." Journal of pharmaceutical sciences 89.7 (2000): 951-957.
Thanou, Maya, et al. "Intestinal absorption of octreotide using trimethyl chitosan chloride: studies in pigs." Pharmaceutical research 18.6 (2001): 823-828.
Tuvia et al. "Oral Octreotide Absorption in Human Subjects: Comparable Pharmacokinetics to Parenteral Octreotide and Effective Growth Hormone Suppression" J Clin Endocrinol Metab (2012) vol. 97, pp. 2362-2369.
Vorobioff, Julio D., et al. "Octreotide enhances portal pressure reduction induced by propranolol in cirrhosis: a randomized, controlled trial." The American journal of gastroenterology 102.10 (2007): 2206-2213.
Williams, G., et al. "Effective and lasting growth-hormone suppression in active acromegaly with oral administration of somatostatin analogue SMS 201-995." The Lancet 328.8510 (1986): 774-778.
Wolf, David C. "The management of variceal bleeding: past, present and future." The Mount Sinai journal of medicine, New York 66.1 (1999): 1-13.
Zidan, J., et al. "Octreotide in the treatment of severe chemotherapy-induced diarrhea." Annals of oncology 12.2 (2001): 227-229.
Jenkins et al. "Randomised trial of octreotide for long term management of cirrhosis after variceal haemorrhage" BMJ (1997)vol. 315, pp. 1338-1341.

\* cited by examiner

ORAL OCTREOTIDE ADMINISTERED IN COMBINATION WITH OTHER THERAPEUTIC AGENTS

RELATED APPLICATIONS

This application is a continuation of U.S. patent application Ser. No. 14/965,318 entitled "ORAL OCTREOTIDE ADMINISTERED IN COMBINATION WITH OTHER THERAPEUTIC AGENTS," filed on Dec. 10, 2015, which claims priority under 35 U.S.C. 119(e) to U.S. Provisional Patent Application Ser. No. 62/090,130 entitled "ORAL OCTREOTIDE ADMINISTERED IN COMBINATION WITH OTHER THERAPEUTIC AGENTS," filed on Dec. 10, 2014, which is hereby incorporated herein by reference in its entirety.

FIELD OF THE TECHNOLOGY

The present invention relates to oral delivery of octreotide in combination with other therapeutic agents for treatment of acromegaly.

BACKGROUND

Combination treatment of injectable octreotide or lanreotide with other therapeutic agents is described in the literature. Examples are Giustina et al (2014) Nature Reviews Endocrinology, vol. 10 pages 243-248; Suda et al (2013) Endocrine Journal, 60 (4), 507-515; Higham et al (2009) Clin Endocrinol. 2009; 71 (1):86-91; and Duarte et al (May 2015) J. Clin Endroclinol Metab, 100(5) 1863-9.

There is a need for use of oral octreotide in combination treatment with other therapeutic agents.

SUMMARY

The present invention relates to combination therapy of a subject suffering from acromegaly. The method of treatment comprises administration to the subject of a therapeutically effective amount of an oral somatostatin receptor ligand (SRL) e.g. oral octreotide in combination with a therapeutically effective amount of a dopamine agonist and/or a growth hormone receptor antagonist and/or a selective estrogen receptor modulator (SERM).

In particular aspects of this invention the dopamine agonist is cabergoline or bromocriptine. In another particular aspect of this invention the growth hormone receptor antagonist is pegvisomant. In another particular aspect of this invention the oral SERM is clomiphene e.g. a clomiphene salt such as clomiphene citrate.

Another aspect of this invention is a unit dosage formulation for oral administration comprising octreotide and a dopamine agonist; in a particular aspect the dopamine agonist is cabergoline. Another aspect of this invention is a unit dosage formulation for oral administration comprising octreotide and a SERM; in a particular aspect the SERM is clomiphene e.g. a clomiphene salt such as clomiphene citrate.

Throughout this application, various publications, including United States patents, are referenced by author and year and patents and applications by number. The disclosures of these publications and patents and patent applications in their entireties are hereby incorporated by reference into this application in order to more fully describe the state of the art to which this invention pertains.

DETAILED DESCRIPTION

Acromegaly is caused by a benign (non-cancerous) tumor (an adenoma) within the pituitary gland that secretes excess growth hormone (GH), leading to elevated levels of insulin-like growth factor-1 (IGF-1). This combined effect of elevated GH and IGF-1 levels causes the enlargement of body parts, including the hands, feet and facial features, along with serious morbidities such as cardiovascular, metabolic and respiratory diseases. If exposed to long-term elevated levels of GH and IGF-1, acromegaly patients face a two- to three-fold increased risk of death.

The current treatment of acromegaly is summarized by Giustina et al 2014, Nature Reviews Endocrinology, vol. 10 pages 243-248, and Adelman 2013, International Journal of General Medicine, 6, 31-38, which are hereby incorporated by reference. Biochemical control of the disease, as measured by both GH and IGF-1 levels, is the primary goal of treatment. Other disease management objectives include tumor shrinkage and improvement in clinical signs and symptoms.

Drug treatment of acromegaly: Currently, several forms of medical therapy are used: Two of these forms of medical therapy are receptor—based, directed at the pituitary adenoma (the somatostatin receptor ligands—SRLs—octreotide, lanreotide and pasireotide which are all given by injection) and the dopamine agonist cabergoline given orally. A third form of medical therapy is directed at blocking GH effects in the periphery (the GH receptor antagonist—GHRA—pegvisomant) given by subcutaneous injection on a daily basis or less frequently e.g. 3 times per week.

SRLs may be given in a "long-acting" formulation (e.g. depot formulation or other slow release formulation) or in a "short-acting" (e.g. immediate release) formulation. The "long-acting" formulation is normally given by means of injection at dosing intervals of four weeks, or alternatively at dosing intervals of 3-8 weeks e.g. at 3, 4, 5, 6, 7, or 8 weeks. The interval between two injections of long-acting SRLs is termed the dosing interval. (Regarding injections, see Chanson 2000, Clinical Endroclinology 53: 577-586; Alexopoulou 2004, European Journal of Endocrinology, 151:317-324; Salvatori 2010, Pituitary 13:115-122; Salvatori Pituitary. 2014; 17(1): 13-21; published online 2013 Jan. 13. doi: 10.1007/s11102-012-0460-2; Melmed 2015, Nature Reviews Endocrinology ibid.) The "short-acting" formulation is normally a subcutaneous injection given daily (or even two or three times a day or more), or may be given 2, 3, 4, 5, or 6 times per week. SRLs were originally termed somatostatin analogs or agonists.

An additional suggested form of medical therapy for acromegaly is to use a selective estrogen receptor modulator (a SERM) e.g. clomiphene; see Duarte et al (2015) ibid. SERMs are normally administered orally.

New potential therapeutic agents for acromegaly are described in Melmed 2015, Nature Reviews Endocrinology, DOI:doi:10.1038/nrendo.2015.196; published online 27 Nov. 2015. These therapeutic agents include the investigational SRL named DG3173 administered by i.m. injection every four weeks; the investigational antisense oligonucleotide named ATL1103, which is a GH receptor antagonist (disrupts GH receptor gene expression) and an investigational long-acting SRL based on octreotide bound in liquid crystal matrix named CAM2029.

Surgery is the primary treatment option if the tumor is resectable. SRLs (injectable octreotide or injectable lanreotide) are the primary first-line treatment after surgery and are the primary treatment option if surgery is not appropriate. Some physicians prescribe dopamine agonists as the primary first-line treatment after surgery. SRLs and dopamine agonists may also be given before surgery.

The aim of treatment is to lower the GH and IGF-1 levels to as close to normal as possible and to improve control of symptoms. Patients who do not respond to injectable SRL therapy (those in whom GH and IGF-1 levels undergo minimal change) or only partially respond (biochemically) to SRL therapy or patients whose acromegaly symptoms are not adequately controlled are often switched to combination therapy: options include (a) injectable SRL plus dopamine agonist (eg cabergoline or bromocriptine); (b) injectable SRL plus growth hormone receptor antagonist (eg pegvisomant); and (c) injectable SRL plus SERM (e.g. clomiphene).

The current invention includes the treatment of acromegaly by treatment with an oral SRL e.g. octreotide in combination with one or more other therapeutic agents. Options include (a) oral SRL plus dopamine agonist e.g. cabergoline or bromocriptine; (b) oral SRL plus growth hormone receptor antagonist e.g. pegvisomant or ATL1103; (c) oral SRL plus a SERM e.g. clomiphene and (d) oral SRL plus injectable SRL. The oral SRL may be oral octreotide, lanreotide or pasireotide or an oral formulation of DG3173. The injectable SRL may be octreotide (eg Sandostatin®), lanreotide (eg Somatuline® Depot in the US and Somatuline® Autogel elsewhere), pasireotide, DG3173 or CAM2019.

A particular case in which the invention may be used is as follows. It may be used with a naïve acromegaly patient who is given oral octreotide in the dosage recommended herein, and thereafter has elevated IGF-1 levels and/or the IGF-1 level has been reduced by 50% of pre-treatment level. Dopamine agonist (an oral therapeutic agent) may be added as combined therapy (i.e. in combination with octreotide). Growth hormone receptor antagonist (such as pegvisomant or ATL1103) may be used instead of dopamine agonist. Alternatively clomiphene may be used in combined therapy with oral octreotide instead of dopamine agonist.

Another particular case in which the invention may be used is as follows. It may be used with a naïve acromegaly patient who is given oral dopamine agonist in the dosage recommended herein, and thereafter has elevated IGF-1 levels the IGF-1 level has been reduced by 50% of pre-treatment level. Oral octreotide may be added as combined therapy (i.e. in combination with dopamine agonist). Growth hormone receptor antagonist (such as pegvisomant) may be used initially instead of dopamine agonist.

Another particular case in which the invention may be used is as follows. It may be used with an acromegaly patient who is already receiving therapy comprising injectable octreotide, lanreotide or pasireotide in combination with dopamine agonist or growth hormone receptor antagonist; the patient switches to oral octreotide instead of injectable octreotide in combination with the dopamine agonist or growth hormone receptor antagonist or SERM.

Other cases in which the invention may be used is in the treatment of naïve patients or patients already treated with parenteral injections who initiate treatment or switch to treatment with the combined therapy of oral octreotide and dopamine agonists.

Another case in which the invention may be used is in the treatment of patients who switch from parenteral injection to oral, and have elevated IGF-1 levels. In this scenario a dopamine agonist or clomiphene or pegvisomant will be added. Oral octreotide therapy in combination with another therapeutic agent as described herein may provide advantages over injectable octreotide combined therapy. These advantages may be better control of IGF-1 and/or hGH levels, or control of IGF-1 and/or hGH levels at lower dosages of medication. In an embodiment, the invention includes the reduction of one or more symptoms of acromegaly such as joint pain, swelling of extremities, headaches, asthenia, sleep apnea and perspiration i.e. improvement in Acromegaly Index of Severity. Particular symptoms include headache, swelling of extremities, joint pain, sweating and fatigue.

Note that using current therapies, in particular long-acting SRLs, biochemical control (i.e. control of IGF-1 and GH) does not necessarily reverse disease-related comorbidities and some symptoms may persist over the long-term despite SRL therapy. Acromegaly symptoms may either occur throughout the dosing interval (the interval between two injections of long-acting SRLs, normally 4 weeks) or recur towards the end of the dosing interval. Leading experts (e.g. Melmed 2015 April J. Clin. Endocrine Metab; 100(4):1699-1708 doi:10.1210/jc.2014-4113; Epub 2015 Feb. 9.) state that some patients report a resurgence of symptoms such as headache toward the end of the dosing interval as the treatment benefit wanes (the so-called "breakthrough" or "wear-off" phenomenon).

Not surprisingly, the effects of disease, its complications, its treatments, and the persistence of symptoms despite therapy have a highly significant negative impact on quality of life parameters (Adelman 2013, ibid).

Breakthrough acromegaly symptoms are common phenomena. A possible intuitive explanation is decline in the pharmacodynamic effects of SRLs towards the end of the dosing interval of the long-acting treatments (see e.g. Melmed, 2015 J. Clin. Endocrine Metab. ibid). As a result, clinicians may prescribe, in addition to the long-acting SRL, daily subcutaneous (sc) SRL and/or schedule long-acting injections at a frequency of less than every 4 weeks to control breakthrough symptoms towards the end of the dosing interval. These additional daily sc injections and/or more frequent long-acting injections may be effective in controlling the breakthrough symptoms, yet significantly increase the physical, emotional, and financial burden of the treatment.

Thus another aspect of the invention is the use of oral octreotide administered in addition to long-acting SRLs or other therapies to prevent or treat breakthrough acromegaly symptoms. This "rescue therapy" may be given on a regular basis towards the end of the four-week dosing interval or on an "as needed basis" when symptoms such as headache or swelling of extremities or any of the acromegaly symptoms recur.

Oral formulations of octreotide have been described, for example in co-assigned US Patent No 8329198 which is hereby incorporated by reference. The oral octreotide may be in a capsule or a tablet. The current invention, which has novel and useful benefits, is an oral formulation of octreotide, in combination with one or more other therapeutic agents.

One aspect of this invention is a method of treatment of a subject suffering from acromegaly which comprises administration to the subject of a therapeutically effective amount of an oral somatostatin receptor ligand (SRL) in combination with a therapeutically effective amount of a dopamine agonist and/or a growth hormone receptor antagonist and/or a $2^{nd}$ somatostatin receptor ligand (SRL) and/or a selective estrogen receptor modulator (SERM). In one aspect of the invention the oral somatostatin receptor ligand (SRL) is octreotide or lanreotide or pasireotide. In a particular aspect of the invention the oral somatostatin receptor ligand (SRL) is octreotide.

In another aspect of this invention the level of IGF-1 in the subject is only partially controlled on octreotide alone. In another aspect of this invention the level of IGF-1 in the subject is only partially controlled on dopamine agonist alone.

In a particular aspect of this invention the dopamine agonist administered in combination with oral octreotide is cabergoline. In another particular aspect of this invention the dopamine agonist is bromocriptine. In another particular aspect of this invention the growth hormone receptor antagonist is pegvisomant.

In particular aspects of this invention the administration of oral octreotide comprises about 5 mg to about 120 mg of octreotide daily, about 40 to about 80 mg of octreotide daily, or about 10 to about 80 mg of octreotide daily, such as 10, 20, 30, 40, 50, 60, 70 or 80 mg daily. A particular dosage of oral octreotide is 80 mg daily. The daily dose of octreotide may be administered in one or two doses a day e.g. the 80 mg daily dose may be administered in two doses of 40 mg each.

In particular aspects of this invention the administration of cabergoline in combination with oral octreotide comprises about 0.2 to about 5 mg of cabergoline weekly; about 0.4 to about 4 mg of cabergoline weekly, such as 1, 2, 3, 3.5 or 4 mg of cabergoline weekly; or about 0.2 to about 1 mg of cabergoline weekly, such as 0.2, 0.40, 0.6 0.8 or 1.0 mg of cabergoline weekly. In certain aspects the administration of cabergoline is bi-weekly, three times weekly or daily.

In a specific aspect, the administration of cabergoline is gradually increased from 0.5 mg×2 per week for first two weeks, 1 mg×2 per week for additional two weeks, followed by 1.5 mg×2 per week for additional two weeks reaching a maintenance dose of 1.75 mg×2 per week.

In particular aspects of this invention the administration of cabergoline is up-titrated to reach a maintenance dose of 3.0 mg to 3.5 mg weekly.

A particular aspect of this invention is a method of treating acromegaly in a subject comprising the following steps: administration of oral octreotide with an initial dose of 20 mg BID; receiving information regarding blood levels of IGF-1 and/or clinical symptoms and in response to blood levels of IGF-1 and/or clinical symptoms, evaluating the course of treatment, wherein if blood levels of IGF-1 are normal and/or clinical symptoms are controlled and/or response level (biochemical and symptomatic response) is maintained, maintain oral octreotide dosage at 20 mg BID; and wherein if IGF-1 levels are increased, or in case of symptomatic exacerbation, dosage of oral octreotide may be adjusted to 60 mg daily (40 mg morning+20 mg evening); continuing to receive information regarding blood levels of IGF-1 and/or clinical symptoms, and evaluating the course of treatment (e.g., applying the above algorithm for maintaining or increasing the dose up to 40 mg BID); wherein if the blood levels of IGF-1 and/or clinical symptoms indicate the subject has failed to respond to octreotide capsules 80 mg for at least two weeks treatment, or subjects having inadequate biochemical control on octreotide capsules 80 mg for at least two weeks treatment, co-administering of octreotide capsules 80 mg with a second therapeutic agent (e.g., a dopamine agonist such as cabergoline or a SERM such as clomiphene). In a specific embodiment the second therapeutic agent is cabergoline, preferably administered up to 3.5 mg/week. In another specific embodiment the cabergoline may be administered twice weekly, preferably with dinner, with a fixed titration algorithm every two weeks, starting with 0.5 mg×2/week at the first two weeks, 1 mg×2/week for additional two weeks, followed by 1.5 mg×2/week, and increase to a maximum of 1.75 mg×2/week. In another specific embodiment the daily dose of cabergoline can be up to 0.5 mg/day (3.5 mg/week), or up to 1 mg×3/week (3.0 mg/week). If IGF-1 is normal and clinical symptoms are controlled or response level (biochemical and symptomatic response) is maintained, continue combination therapy In particular aspects of this invention the administration of pegvisomant in combination with oral octreotide comprises about 2 mg to about 60 mg of pegvisomant daily, about 10 to about 20 mg of pegvisomant daily; or about 2 to about 10 mg of pegvisomant daily, such as 2, 4, 6, 8 or 10 mg of pegvisomant daily. The pegvisomant may be administered one or twice or three times or four times or five times or six times per week in these daily amounts. In an embodiment the pegvisomant is administered three times per week.

A particular aspect of this invention is a method of treatment of a subject suffering from acromegaly which comprises administration to the subject a therapeutically effective amount of oral octreotide in combination with a therapeutically effective amount of a SERM. In a specific aspect the SERM is clomiphene. Other SERMs of this invention include tamoxifen and raloxifen. In further aspects the administration of octreotide comprises about 5 mg to about 120 mg of octreotide daily or about 40 to about 100 mg of octreotide daily or 80 mg of octreotide daily. In further aspects the administration of clomiphene comprises 10-200 mg per day or in particular about 50 mg per day. Estrogens may also be used in combination with oral SRLs, in particular for women.

Another aspect of this invention is a method of treatment of a subject suffering from acromegaly which comprises administration to the subject of a therapeutically effective amount of an oral somatostatin receptor ligand (SRL) in combination with a therapeutically effective amount of a dopamine agonist and/or a growth hormone receptor antagonist and/or a $2^{nd}$ somatostatin receptor ligand (SRL) and/or a selective estrogen receptor modulator (SERM) wherein the oral somatostatin receptor ligand (SRL) is octreotide or lanreotide or pasireotide and wherein the $2^{nd}$ somatostatin receptor ligand (SRL) is a long-acting injectable formulation. In a particular aspect of the invention the subject is treated with oral octreotide and with a $2^{nd}$ somatostatin receptor ligand (SRL) which is a long-acting injectable formulation, which may be administered every 4 weeks, or every 3-6 weeks or every 3, 4, 5, or 6 weeks. In a particular aspect of the invention the administration of oral octreotide in addition to the long-acting SRL is in order to control breakthrough acromegaly symptoms. In another aspect the administration of oral octreotide comprises about 10 to about 80 mg of octreotide daily, such as 10, 20, 30, 40, 50, 60, 70 or 80 mg daily. In another aspect the octreotide is administered on an "as needed" basis to control breakthrough acromegaly symptoms. In other aspects the octreotide is administered on a regular basis e.g. on a daily basis. In a particular aspect the octreotide is administered on a daily basis toward the end of the month wherein the long-acting somatostatin receptor ligand was administered. In another particular aspect the octreotide is administered during the fourth week after the long-acting somatostatin receptor ligand was administered, preferably on a daily basis.

Another aspect of this invention is a unit dosage formulation for oral administration comprising a SRL and a dopamine agonist; in a particular aspect the SRL is octreotide and in another particular aspect the dopamine agonist is cabergoline. In another particular aspect this unit dosage formulation comprises 5-120 mg octreotide, in particular 20 mg octreotide. In another particular aspect this unit dosage formulation comprises 5-120 mg octreotide and 0.01-1.0 mg cabergoline.

Another aspect of this invention is a unit dosage formulation for oral administration comprising an SRL and a SERM; in a particular aspect the SRL is octreotide; in another particular aspect the SERM is clomiphene. In one aspect the unit dosage formulation comprises 5-120 mg octreotide and clomiphene. In another aspect the unit dosage formulation comprises 5-120 mg octreotide and 5-200 mg clomiphene. In a specific aspect the unit dosage formulation comprises 20 mg octreotide.

Another aspect of this invention is a unit dosage formulation for oral administration comprising an SRL and a dopamine agonist and a SERM i.e. three active pharmaceutical ingredients (APIs). In a specific aspect the SRL is octreotide. In another aspect the dopamine agonist is cabergoline. In another aspect the SERM is clomiphene. In another aspect the dopamine agonist is cabergoline and the SERM is clomiphene. Further aspects of this "triple API" unit dosage formulation comprise 5-120 mg octreotide. Other aspects of this "triple API" unit dosage formulation comprise 0.01-1.0 mg cabergoline. Other aspects of this triple API unit dosage formulation comprise 5-200 mg clomiphene. A particular aspect of this triple API unit dosage formulation comprises 5-120 mg octreotide, 0.01-1.0 mg cabergoline and 5-200 mg clomiphene. In a specific aspect this triple API unit dosage formulation comprises 20 mg octreotide.

Another aspect of this invention is a method of treatment of a subject suffering from acromegaly which comprises administration to the subject a therapeutically effective amount of an SRL in combination with a therapeutically effective amount of a dopamine agonist and/or a growth hormone receptor agonist and/or a SERM; in particular aspects the oral SRL is selected from octreotide, lanreotide and pasireotide (SOM-230). In a particular aspect the dopamine agonist is cabergoline. In another particular aspect the dopamine agonist is bromocriptine. In another particular aspect the growth hormone receptor antagonist is pegvisomant. In another particular aspect the SERM is clomiphene.

Octreotide is a cyclic octapeptide (e.g. a salt such as acetate or chloride) and is an analog (agonist) of the natural hormone somatostatin; it mimics somatostatin pharmacologically, though it is a more potent inhibitor of growth hormone, glucagon and insulin than the natural hormone. The molecular weight of octreotide is 1019.3 (free peptide, C49H66N10O10S2). Injectable octreotide is sold commercially as Sandostatin® which is a short-acting formulation administered sc and Sandostatin® LAR, which is a long-acting formulation administered by intramuscular (im) injection.

In an embodiment, oral octreotide in the following formulations is disclosed and claimed in co-assigned U.S. Pat. No. 8,329,198; see for example claims 1-26.

Oral octreotide for clinical trials is provided as an enteric-coated capsule containing 20 mg of octreotide (20 mg calculated as free base), polyvinylpyrrolidone (PVP-12), sodium caprylate, magnesium chloride, polysorbate 80, glyceryl monocaprylate, glyceryl ricaprylate, gelatin, gelatin capsules and Acryl-EZE® (methacrylate). The pharmaceutical compositions described herein include incorporation of octreotide as a therapeutic agent within an oral dosage form which is enteric-coated. An oral dosage form according to the invention comprises additives or excipients that are suitable for the preparation of the oral dosage form according to the present invention. The oral dosage form may comprise tablets or capsules, preferably enteric-coated.

Other SRLs are lanreotide (eg Somatuline® Depot in the US and Somatuline® Autogel elsewhere) which is a cyclic octapeptide, and pasireotide (Signifor®; SOM-230) which is a cyclic hexapeptide and is currently approved for $2^{nd}$ line therapy and in clinical trials. Somatuline® Depot is a long-acting formulation and Signifor® is a short-acting formulation which may be administered subcutaneously once or twice a day or more.

Cabergoline tablets contain cabergoline, a dopamine receptor agonist. The chemical name for cabergoline is 1-[(6-allylergolin-8β-yl)-carbonyl]-1-[3-(dimethylamino) propyl]-3-ethylurea. Its molecular formula is C26H37N5O2, and its molecular weight is 451.62.

Pegvisomant (trade name Somavert®) is a growth hormone receptor antagonist. Pegvisomant is a protein containing 191 amino acid residues to which several polyethylene glycol polymers have been covalently bound in order to slow clearance from the blood. The protein is a modified version of human growth hormone designed to bind to and block the growth hormone receptor. It is manufactured using genetically modified *E. coli* bacteria. The polyethylene glycol polymers are subsequently added chemically. This is a short-acting formulation which is administered by subcutaneous injection given daily (or even two or three times daily or more). It may also be administered or once, twice, three, four, five or six times per week e.g. when used in combination therapy.

Clomiphene is a selective estrogen receptor modulator (a SERM) i.e. it is a competitive inhibitor of estrogen binding to estrogen receptors (ERs) and has mixed agonist and antagonist activity, depending upon the target tissue. It has several trade names including Androxal®, Clomid® and Omifin®. Chemically, clomiphene is a non-steroidal triphenylethylene derivative. As currently manufactured, clomiphene is a mixture of two geometric isomers, enclomifene (E-clomifene) and zuclomifene (Z-clomifene). These two isomers have been found to contribute to the mixed estrogenic and anti-estrogenic properties of clomiphene. The use of clomiphene in methods of this invention may be in male and female subjects.

Administered "in combination", as used herein, means that two (or more) different therapeutic agents are delivered to the subject during the course of the subject's affliction with the disorder, e.g., the two or more therapeutic agents are delivered after the subject has been diagnosed with the disorder and before the disorder has been cured or eliminated or treatment has ceased for other reasons. In some embodiments, the delivery of one therapeutic agent is still occurring when the delivery of the second begins, so that there is overlap in terms of administration. This is sometimes referred to herein as "simultaneous" or "concurrent delivery". In other embodiments, the delivery of one therapeutic agent ends before the delivery of the other treatment begins. In some embodiments of either case, the therapeutic agents are more effective because of combined administration. For example, the second therapeutic agent is more effective, e.g., an equivalent effect is seen with less of the second therapeutic agent, or the second therapeutic agent reduces symptoms to a greater extent, than would be seen if the second therapeutic agent were administered in the absence of the first therapeutic agent, or the analogous situation is seen with the first therapeutic agent. In some embodiments, delivery is such that the reduction in a symptom, or other parameter related to the disorder is greater than what would be observed with one therapeutic agent delivered in the absence of the other. The effect of the two therapeutic agents can be partially additive, wholly additive, or greater than additive. The delivery can be such that an effect of the first therapeutic agent delivered is still detectable when the second is delivered.

The compositions described herein can be administered to a subject i.e., a human or an animal, in order to treat the subject with a pharmacologically or therapeutically effective amount of a therapeutic agent described herein. The animal may be a mammal e.g., a mouse, rat, pig, dog horse, cow or sheep. As used herein the terms "pharmacologically effective amount" or "therapeutically effective amount" or "effective amount" means that amount of a drug or pharmaceutical agent (the therapeutic agent) that will elicit the biological or medical response of a tissue, system, animal or human that is being sought by a researcher or clinician and/or halts or reduces the progress of the condition being treated or which otherwise completely or partly cures or acts palliatively on the condition, or prevents development of the condition.

As used herein, the term "treatment" as for example in "method of treatment" or "treat" or "treating" refers to therapeutic treatment, wherein the object is to reduce or reverse or prevent the symptoms of a disease or disorder. In some embodiments, the compounds or compositions disclosed herein are administered prior to onset of the disease or disorder. In some embodiments, the compounds or compositions disclosed herein are during or subsequent to the onset of the disease or disorder.

The function and advantages of these and other embodiments will be more fully understood from the following examples. These examples are intended to be illustrative in nature and are not to be considered as limiting the scope of the systems and methods discussed herein.

EXAMPLES

Example 1: Clinical Experiments on Combined Treatments Using Oral Octreotide a. Oral octreotide and cabergoline. The effect of combined treatment of oral octreotide with cabergoline is studied and compared with the combined treatment of octreotide (injectable) with cabergoline. This is performed as described in the literature except that oral octreotide replaces injectable octreotide. See for example Giustina et al (2014) Nature Reviews Endocrinology, vol. 10 pages 243-248 and Suda et al (2013) Endocrine Journal, 60(4), 507-515. Oral octreotide is administered at 10, 20, 40, 60 or 80 mg dose. Patients who fail to respond to octreotide capsules 80 mg (40 mg, twice daily) for at least two weeks therapy or patients having inadequate biochemical control (with IGF-1≥1.3×ULN to IGF-1<2×ULN) can receive co-administration of octreotide capsules 80 mg with cabergoline (up to 3.5 mg/week). In certain circumstances patients can receive less oral octreotide e.g. 40 or 60 mg daily in combination with cabergoline. Cabergoline is administered twice weekly, preferably with dinner, with a fixed titration algorithm every two weeks, starting with 0.5 mg×2/week at the first two weeks, 1 mg×2/week for additional two weeks, followed by 1.5 mg×2/week, and increase to a maximum of 1.75 mg×2/week. In case of intolerance, the dose may be either maintained or reduced to the prior dose level for two weeks followed by attempts, per the physician's discretion, to up-titrate. On a case-by-case basis, daily doses can be considered up to 0.5 mg/day (3.5 mg/week), or up to 1 mg×3/week (3.0 mg/week), to improve tolerability or compliance.

b. Oral octreotide and pegvisomant. The effect of combined treatment of oral octreotide with pegvisomant is studied and compared with the combined treatment of octreotide (injectable) with pegvisomant or compared with octreotide alone. This is performed as described in the literature except that oral octreotide replaces injectable octreotide. See for example Giustina et al (2014) Nature Reviews Endocrinology, vol. 10 pages 243-248 and Higham et al (2009) Clin Endocrinol. 2009; 71 (1):86-91 Oral octreotide is administered at 10, 20, 40, 60 or 80 mg dose once or twice daily.

c. Oral octreotide and cabergoline and pegvisomant. The effect of combined treatment of oral octreotide with both cabergoline and pegvisomant is studied and compared with the combined treatment of octreotide (injectable) with both cabergoline and pegvisomant or compared with octreotide alone. This is performed as described in the literature cited above except that oral octreotide replaces injectable octreotide. Oral octreotide is administered at 10, 20, 40, 60 or 80 mg dose once or twice daily.

d. Oral octreotide with clomiphene. The effect of combined treatment of oral octreotide with clomiphene is studied and compared with the combined treatment of octreotide (injectable) and clomiphene or compared with octreotide alone. This is performed as described in Duarte et al (May 2015) J. Clin Endroclinol Metab, 100 (5) 1863-9 except that oral octreotide replaces injectable octreotide. Oral octreotide is administered at 10, 20, 40, 60 or 80 mg dose given once or twice daily.

e. Oral octreotide with clomiphene and cabergoline. The effect of combined treatment of oral octreotide with clomiphene and cabergoline is studied and compared with the combined treatment of octreotide (injectable) and clomiphene and cabergoline or compared with octreotide alone. This is performed as described in the literature cited above except that oral octreotide replaces injectable octreotide. Oral octreotide is administered at 10, 20, 40, 60 or 80 mg dose given once or twice daily.

Having thus described several aspects of at least one embodiment, it is to be appreciated that various alterations, modifications, and improvements will readily occur to those skilled in the art. Such alterations, modifications, and improvements are intended to be part of this disclosure and are intended to be within the scope of the invention. Accordingly, the foregoing description is by way of example only, and the scope of the invention should be determined from proper construction of the appended claims, and their equivalents.

The invention claimed is:

1. A method of treating acromegaly in a subject in a subject who has failed to respond to oral octreotide capsules 80 mg daily for at least two weeks treatment, or has inadequate biochemical control on octreotide capsules 80 mg daily for at least two weeks treatment such that the subject's blood levels of IGF-1 are at least 1.3 times the upper limit of normal to two times the upper limit of normal, wherein the octreotide is co-administered at 40, 60 or 80 mg daily with cabergoline at up to 3.5 mg per week.

2. The method of claim 1 wherein the cabergoline may be administered twice weekly, preferably with dinner, with a fixed titration algorithm every two weeks, starting with 0.5 mg×2/week at the first two weeks, 1 mg×2/week for additional two weeks, followed by 1.5 mg×2/week, and increase to a maximum of 1.75 mg×2/week.

3. The method of claim 1 wherein the daily dose of cabergoline can be up to 0.5 mg/day, or up to 1 mg×3/week.

* * * * *